United States Patent [19]

Paborji et al.

US005216011A

[11] Patent Number: 5,216,011
[45] Date of Patent: Jun. 1, 1993

[54] STABLE SOLUTIONS OF MITOMYCIN C

[75] Inventors: Mehdi Paborji, Liverpool; Joseph B. Bogardus, Manlius; Shreeram N. Agharkar, Fayetteville; William P. Coppola, Canastota, all of N.Y.

[73] Assignee: Bristol-Myers Squibb Co., New York, N.Y.

[21] Appl. No.: 401,713

[22] Filed: Sep. 1, 1989

[51] Int. Cl.$^5$ .............................................. A61K 31/40
[52] U.S. Cl. .................................................... 514/410
[58] Field of Search ........................................ 514/410

[56] References Cited

FOREIGN PATENT DOCUMENTS 7203008 8/1981 Japan .
0258114 5/1984 Japan .
2114885 9/1983 United Kingdom .

OTHER PUBLICATIONS

Hoffman, CA 104:56438g 1985.
Konishi CA 110:63733b 1988.
Kawata, CA 99:218581f 1983.

Primary Examiner—Frederick E. Waddell
Assistant Examiner—Russell Travers
Attorney, Agent, or Firm—Sandra M. Nolan

[57] ABSTRACT

A stable solution of mitomycin C in propylene glycol or propylene glycol/water is disclosed. The solutions have an acceptable shelf-life of greater than 24 months at 4° C. and can be injected directly or diluted with water or other aqueous parenteral vehicle for parenteral administration.

6 Claims, No Drawings

STABLE SOLUTIONS OF MITOMYCIN C

BACKGROUND OF THE INVENTION

1. Field of the Invention

The present invention relates to stable solutions of mitomycin C which may be injected directly or diluted with sterile water or other suitable diluent for parenteral administration.

2. Description of the Prior Art

Mitomycin C is an antineoplastic antibiotic which is isolated from the fermentation of *Streptomyces caespitosus*. It is administered parenterally for the treatment, inter alia, of gastric carcinoma, pancreatic carcinoma, breast carcinoma, head and neck carcinoma, biliary carcinoma, lung carcinoma, bladder carcinoma and cervical carcinoma.

Mitomycin C is currently being marketed by Bristol-Myers Company under the tradename Mutamycin ® as a lyophilized dosage form containing mannitol. Vials containing 20 and 40 mg mitomycin C are reconstituted with Sterile Water for Injection at 0.5 mg/ml and the reconstituted solutions are reported to be stable for 7 days at room temperature or 14 days under refrigeration.

It would be desirable to have a solution form of mitomycin C which would not require reconstitution prior to use. Improper reconstitution of a lyophilized product sometimes results in the formation of air-borne droplets ("blow-back") which, in the case of a potent antitumor agent such as mitomycin C, may be a health hazard to the personnel making up the solution for injection. Also, production of the present lyophilized mitomycin C product is quite costly, and a solution dosage form would be expected to have a lower cost of goods.

The stability and mechanisms of degradation of mitomycin C and its analogs in aqueous solutions have been the subject of many investigations[1-11]. Degradation in aqueous solutions is affected by acidic or alkaline pH, buffers and temperature. At pH below 7, mitomycin C is converted to 1-hydroxy-2,7-diaminomitosanes, and at pH above 7 it is hydrolyzed to 7-hydroxymitosane. Maximum stability is observed at about pH 7–8. In water at 25° C., mitomycin C loses 10% potency in about 40 days. Diluted in i.v. fluids at room temperature to a concentration of 20–40 mcg/mL, it is stable for the following times: 5% dextrose injection, 3 hours; 0.9% sodium chloride injection, 12 hours; sodium/lactate injection, 24 hours[12].

These data suggest that formulation of a ready-to-use aqueous solution of mitomycin C would be impossible, even when stored under refrigeration. The present inventors have found no report of the stability of mitomycin C in non-aqueous solvents suitable for parenteral administration. Since the prior art teaches that water rapidly induces mitomycin C degradation, however, one would expect that optimum stability would only be possible in solvents with very low water content.

U.S. Pat. No. 4,684,630 describes a method of parenterally delivering aqueous-unstable drugs which includes the aqueous dilution of a stable, anhydrous organic solution having the drug dissolved therein. Methods for preparation of stable solutions of the anticancer drugs, 5-azacytosine arabinoside and 5-azacytidine, are disclosed in which anhydrous solutions in dimethylsulfoxide or dimethylacetamide are diluted with an aqueous solution immediately prior to intravenous injection. There is no disclosure, however, of mitomycin C solutions.

It is an object of the present invention to provide a mitomycin C solution dosage form which is stable (≦10% potency loss) for at least two years under refrigeration (4° C.) and which can be injected directly or diluted with water or other aqueous vehicle for parenteral administration.

SUMMARY OF THE INVENTION

The present invention provides a stable solution of mitomycin C suitable for injection or dilution with water or other aqueous vehicle for parenteral administration, said solution comprising mitomycin C in a solvent medium consisting of about 40–100% (v/v) of propylene glycol and about 0–60% (v/v) water.

DETAILED DESCRIPTION

Mitomycin C has a solubility in water at 25° C. of about 0.9 mg/mL. Thus, preparation of an aqueous solution form of mitomycin C at a significantly higher concentration than the present 0.5 mg/mL reconstituted lyophile is not feasible, especially if refrigerated storage is contemplated.

Mitomycin C (MMC) was found by the present inventors to have a higher solubility in a number of organic solvents (see Table I below). The solubility was determined by adding known aliquots of the solvents to accurately weighed samples of MMC with Vortex mixing and sonication until MMC dissolved or a concentration less than 0.5 mg/mL was reached. Solubilities greater than 5 mg/mL were observed in several solvents and solubilities greater than 50 mg/mL were observed in dimethylsulfoxide, 1-methyl-2-pyrrolidinone and N,N-dimethylacetamide.

TABLE I

Approximate solubility of mitomycin C in various vehicles at room temperature (22–24° C.)

| Solvent | Approximate Solubility, mg/mL |
| --- | --- |
| Benzyl benzoate | <0.5 |
| Benzyl alcohol | 7 |
| Miglyol 818 | <0.5 |
| Miglyol 840 | <0.5 |
| Dimethyl sulfoxide | >50 |
| Ethanol | 2 |
| Polyethylene Glycol 200 | 7 |
| Polyethylene Glycol 300 | 7 |
| Polyethylene Glycol 400 | 6 |
| Propylene glycol | 7 |
| Glycerin | 8 |
| 1-methyl-2-pyrrolidinone[a] | >60 |
| 2-pyrrolidinone[a] | >40 |
| N,N-dimethylacetamide | >100 |

[a]The pH of these vehicles was adjusted to 7 with citric acid.

The equilibrium solubility of mitomycin C in propylene glycol and propylene glycol/water mixtures after 48 hours equilibration is shown in Table II. In neat propylene glycol at 25° C., the solubility of mitomycin C was about 10 mg/mL. In 60–90% propylene glycol/water mixtures, the solubility unexpectedly increased to about 13–16 mg/mL. Below 60% propylene glycol, mitomycin C solubility decreased as the water content increased. Because of the higher mitomycin C solubility with addition of water, 5 mg/mL mitomycin C solutions in propylene glycol do not crystallize on storage for several months at −15° C. or 4° C. Addition of water to propylene glycol also has the benefit of reducing the viscosity of the preparation and improving its syringeability, especially when cold.

TABLE II

Equilibrium solubility of mitomycin C in propylene glycol/water mixtures at 25° C.

| Solvent | pH | Solubility[b] mg/mL | Concentration[c] mg/mL |
|---|---|---|---|
| 100% Propylene Glycol (PG) | 7.44 | 10.4 | 10.3 |
| 90% PG/Water | 7.65 | 13.9 | 13.8 |
| 80% PG/Water | 7.53 | 15.1 | 15.1 |
| 70% PG/Water | 7.29 | 16.5 | 15.8[d] |
| 60% PG/Water | 7.20 | 15.3 | 11.6[d] |
| 50% PG/Water | 7.22 | 12.0 | 5.8[d] |
| Water | 7.30 | 2.4 | 0.6[d] |

[a]Equilibration was for 48 hours in sealed vials on a Vibromixer and in a constant temperature water bath at 25° C.
[b]Analysis by HPLC.
[c]Concentration of the 48 hour solutions after standing additional 4 days at 5° C. and filtered (nylon filter, 0.45 micron).
[d]Precipitate found in these samples after 4 days at 5° C.

The kinetics and mechanism of degradation of mitomycin C in aqueous solutions have been the subject of several investigations, as described above in the prior art section. An analysis of kinetic data from the literature is shown in Table III. In water, we find that mitomycin C potency falls to 90% of its original value after only 40 days at 25° C. Using these data and the reported Arrhenius activation energy, the predicted $t_{90}$ for mitomycin C at 5° C. in unbuffered aqueous solution was calculated to be about one year. Thus, formulation of an aqueous injectable solution of mitomycin C with a minimally acceptable shelf life of 18 months would not appear feasible, even when the product would be stored under refrigeration.

TABLE III

Predicted stability of mitomycin C at different temperatures
$E_{act} = 19.4$ Kcal/mol[a]

| Temp, °C. | $k_{cal}$, h$^{-1}$ | $t_{50}$, y | $t_{90}$ |
|---|---|---|---|
| 25 | 1.10E-04[b] | 0.7 | 40 d |
| 5 | 1.04E-05 | 7.6 | 420 d |

[a]Activation energy for decomposition of mitomycin C at neutral pH in unbuffered solution from Ref. 6. h:hour; d:day; y:year.
[b]Experimentally measured rate constant for decomposition of mitomycin C in 0.05M phosphate buffer, pH 7.43.

Stability data obtained with mitomycin C in various non-aqueous solvents of solvent/water mixtures are shown in Tables IV–VII. As shown in Table IV, mitomycin C exhibited poor and variable stability in three molecular weight grades of polyethylene glycol (PEG'S 200, 300 and 400). In PEG 400, purging with nitrogen improved stability. This is consistent with the known tendency of PEG'S to form peroxides on storage. Additionally, the effect of the antioxidant, propyl gallate, was found not to improve stability in nitrogen purged solutions. An attempt to improve stability by adjustment of pH to 6.2 (measured after 1:1 dilution with water) using sodium glycodeoxycholate was also unsuccessful. Due to the poor stability, PEG'S were concluded to be unacceptable solvents for mitomycin C solutions/formulations.

Stability of mitomycin C in several other solvents is shown in Table V. Excellent stability was observed in N,N-dimethylacetamide (DMA), 1-methyl-,2-pyrrolidinone (NMP) and propylene glycol (PG). Slightly lower stability was found with 2-pyrrolidone (2-Pyr), but stability in ethanol (in which solubility is also low) was surprisingly poor. The results in ethanol were unexpected in view of the propylene glycol data because of the chemical and structural similarities of the two solvents. In view of the aqueous instability of mitomycin C, it was especially surprising to find that addition of 2% water appeared to increase stability compared to the neat solvent. These data indicate that great care would not be required to prevent moisture pick-up in the preparation and handling of mitomycin C formulations in propylene glycol.

TABLE IV

Stability of mitomycin C (5 mg/mL) in polyethylene glycols[a]

| | Percent Remaining | | | | |
|---|---|---|---|---|---|
| | PEG 200 | PEG 300 | PEG 400 | | |
| Conditions | N$_2$ | N$_2$ | N$_2$ | Air | pH adjusted[b] |
| 1 wk/45° C. | 57.1 | 78.6 | 62.8 | 48.2 | 68.3 |
| 2 wks/37° C. | 53.7 | 81.2 | 61.4 | 38.7 | 66.7 |

[a]Solutions were kept in amber vials, purged with nitrogen and closed with 1888 gray butyl stoppers and aluminum seals.
[b]pH adjusted to 6.2 with sodium glycodeoxycholate.

TABLE V

Solution stability of mitomycin C in non-aqueous solvents[a]

| | | Percent Remaining | |
|---|---|---|---|
| Solvent | mg/mL | 12 wks 37° C. | 12 wks 25° C. |
| DMA | 4.77 | 92.7 | 106.5 |
| NMP[b] | 4.93 | 90.9 | 99.6 |
| 2-Pyr[b] | 4.44 | 74.5 | 91.0 |
| PG[c] | 4.82 | 90.9 | 95.9 |
| PG/water 98/2 (v/v) | 4.58 | 94.3 | 99.1 |
| EtOH | 2.31[d] | 22.5 | 76.2 |

DMA: dimethylacetamide; NMP: 1-methyl-2-pyrrolidinone; 2-Pyr: 2-pyrrolidinone; PG: propylene glycol; EtOH: absolute ethanol.
[a]All solutions on test in amber vials and nitrogen purged.
[b]The pH of these vehicles was adjusted to 7.0 with citric acid.
[c]Dried over molecular sieve.
[d]Low original assay believed due to solubility.

TABLE VI

Stability of mitomycin C in non-aqueous solutions[a]

| Time/ Temp. (°C.) | water[b] | PG | Percent Remaining | | | Glycerin |
|---|---|---|---|---|---|---|
| | | | 95% PG | 90% PG | 50% PG | |
| 2 wks/40 | 40.2 | 93.6 | 92.9 | 90.1 | 89.0 | 0.15 |
| 1 mo/40 | 14.1 | 91.2 | 89.8 | 87.2 | 90.2 | — |
| 3 mo/40 | — | 77.0 | 76.1 | 76.5 | — | — |
| 1 mo/25 | | 99.0 | 99.0 | 98.6 | | 54.7 |
| 3 mo/25 | | 99.4 | 98.1 | 99.0 | | 12.6 |
| 6 mo/25 | | 85.6 | 90.2 | 89.3 | | 0.0 |
| 12 mo/25 | | 71.9 | 81.5 | 84.1 | | — |
| 1 mo/25/Air[c] | | 97.5 | 97.3 | 97.3 | | 92.4 |
| 3 mo/25/Air | | 94.3 | 97.1 | 98.6 | | 55.8 |
| 6 mo/25/Air | | 68.8 | 86.3 | 88.0 | | 38.8 |
| 12 mo/25/Air | | 30.6 | 70.3 | 79.0 | | — |
| 1 mo/4 | | 100.4 | 101.0 | 100.2 | | 93.5 |
| 3 mo/4 | | 102.5 | 103.3 | 103.9 | | 80.9 |
| 6 mo/4 | | 98.6 | 100.0 | 99.2 | | 39.9 |
| 12 mo/4 | | 94.7 | 96.0 | 93.8 | | — |
| 1 mo/4/Air[c] | | 101.4 | 100.6 | 100.6 | | 95.7 |
| 3 mo/4/Air | | 100.8 | 101.9 | 104.1 | | 97.5 |
| 6 mo/4/Air | | 97.3 | 97.9 | 98.8 | | 83.5 |
| 12 mo/4/ | | 89.7 | 95.4 | 96.3 | | 54.7 |

TABLE VI-continued

Stability of mitomycin C in non-aqueous solutions[a]

| Time/Temp. (°C.) | water[b] | PG | Percent Remaining 95% PG | 90% PG | 50% PG | Glycerin |
|---|---|---|---|---|---|---|
| Air | | | | | | |

[a] Concentration of solutions, 5 mg/mL except for glycerin solution which had a solubility of only 2.78 mg/mL.
[b] Mitomycin C concentration was 0.5 mg/mL because of its low solubility in water.
[c] All solutions stored under nitrogen except where air is noted.

TABLE VII

Pseudo first-order rate constants for degradation of mitomycin C in neat propylene glycol[a]

| T,°C. | T, K | 10²ko, m⁻¹ | t90 |
|---|---|---|---|
| 4 | 277 | 0.276 | 38 months (39 m[b]) |
| 25 | 298 | 2.69 | 3.9 months |
| 40 | 313 | 8.40 | 37 days |

[a] Data were taken from Table VI. m:month.
[b] Predicted from 40° C. data.

Although dimethylacetamide, N-methylpyrrolidinone and 2-pyrrolidionine appear to be suitable solvents for a mitomycin C solution dosage form, all of these solvents are considered questionable for human use based on toxicological concerns. For use in mitomycin C formulations, these concerns are especially serious because of the relatively large amount of solvent needed for drug solubilization and stabilization. Propylene glycol, however, which also shows an excellent solubility and stability profile with mitomycin C, has a long record of safe use in numerous human injectable products.

Table VI shows additional stability data for mitomycin C in propylene glycol, water/propylene glycol mixtures, and glycerin. These data confirm the results of the previous study and show that 5% and 10% water do not adversely affect, and may actually improve, mitomycin C stability. Excellent stability is also shown for all the PG formulations at 25° C., and 4° C. In the PG and water/PG formulations, the solutions were visually observed to be unchanged from initial and free of particulate matter or crystallization of mitomycin C.

The poor stability in glycerin is in strong contrast with PG or PG/water data in Table VI. This is surprising because of the close structural similarity between PG and glycerin.

Using stability data in Table VI for the mitomycin C solution in neat propylene glycol at 4° C., 25° C. and 40° C., pseudo-first order rate constants and t90 values shown in Table VII were calculated by linear regression analysis of plots of log (% remaining) vs. time. The logarithms of the rate constants were then plotted vs 1/T to obtain the Arrhenius activation energy, Ea=16.5 Kcal/mole. Both actual (Table VI) and predicted data (from regression analysis) indicate that potency will remain greater than 90% of initial for more than 30 months at 4° C., the intended storage temperature. Since it is conventional to have a margin of acceptability in assigning shelf life, it is an object of this invention to provide a mitomycin C solution formulation with a shelf life of at least 24 months. Since mitomycin C stability is not adversely affected by 5-10% water in propylene glycol and may even be improved (Table VI), an equivalent stability prediction can be made for these PG/water systems.

In an attempt to improve the stability of mitomycin C in propylene glycol, the effect of three antioxidants was compared to a control solution of mitomycin C in PG. The results indicate that these antioxidants do not significantly improve mitomycin C stability in propylene glycol. The effect of air vs. nitrogen on stability of MMC was also investigated at 25° C. As shown in Table VI, MMC appears more stable in the presence of nitrogen. Interestingly, the difference in stability appears to diminish as the water content of PG/water mixtures increases.

Efforts were also made to improve the stability of mitomycin C in propylene glycol by pretreatment of propylene glycol prior to its use. The effect of pretreatment of propylene glycol with sodium bicarbonate and carbon (Darco G-60) was investigated. The results indicate that mitomycin C stability was significantly improved by pretreatment of propylene glycol with sodium bicarbonate. However, pretreatment of propylene glycol with carbon (Darco G-60) did not significantly improve mitomycin C stability. Pretreatment of propylene glycol with other pharmaceutically acceptable bases such as sodium carbonate, N-methyl-d-glucamine, lysine and arginine can also be employed to enhance stability in the same manner as with $NaHCO_3$.

After extensive testing it has been concluded that propylene glycol is unique among pharmaceutically acceptable solvents in providing good solubility and stability of mitomycin C. The superior stability of mitomycin C in PG or water/PG compared to other hydroxylic solvents such as ethanol, glycerin and polyethylene glycols and its insensitivity to water are completely unexpected and would not have been predicted from the prior art.

The concentration of mitomycin C used in the present solutions is not critical and can vary over a wide range, e.g. from about 0.5 mg/mL to about 12 mg/mL. The preferred concentration of mitomycin C, however, is about 5 mg/mL which would require a 1:10 dilution with a suitable parenteral diluent, such as sterile water, 0.9% sodium chloride, or the like, to reach the 0.5 mg/mL concentration utilized in prior art reconstituted mitomycin C solutions. The solution can also be administered by slow injection into a freely flowing i.v. infusion, as is also commonly practiced with prior art mitomycin C compositions at 0.5 mg/mL. In either case, this higher concentration allows the user to handle a much smaller volume of this cytotoxic drug, which is advantageous from the standpoint of personnel safety. Since the product must be stored under refrigeration, the resulting smaller container conserves expensive refrigerator space. If the product is diluted before administration, the concentration of PG after dilution is sufficiently low to result in good venous toleration and lack of side effects. Slow injection of the undiluted solution is also well-tolerated because of the dilution factor of the i.v. infusion.

The mitomycin C may be added to neat propylene glycol or to propylene glycol/water mixtures having up to 60% water. The preferred solutions have a solvent medium consisting of about 50-80% propylene glycol and 20-50% water. As noted above, the stability of mitomycin C decreases slowly as the water content increases while the solubility increases with higher proportions of water until it reaches its maximum, then decreases. By proper adjustment of mitomycin C concentration and water content, however, solutions of mitomycin C concentrations within the range of 5-12 mg/mL and water contents of from 0-50% can be obtained which are stable for at least two years at 4° C.

Although not essential to produce the invention, other pharmaceutically acceptable ingredients may be present such as buffers, antioxidants, surfactants, stabilizers, preservatives, etc. The solutions of the present invention retain 97-99% potency over a period of three months at 25° C. and are expected to be stable for two years or more under refrigeration (4° C.).

The diluted solutions of mitomycin C according to the present invention may be used for the treatment of cancer in the same manner as the present commercial reconstituted lyophilized form. Commonly used routes of administration of mitomycin C include intravenous, intraarterial, intracavitary, intravesical, etc. The solutions may also be used without dilution for slow intravenous injection, e.g. into a freely flowing infusion of 0.9% sodium chloride or 5% dextrose, or as convenient concentrates in infusion pump systems for prolonged infusion.

The solutions of the present invention may be prepared by dissolving the desired components in propylene glycol or propylene glycol/water. The resulting solution is then suitably filtered and the filtrate collected.

The following examples serve to illustrate the present invention without limiting its scope.

EXAMPLE 1

Into a 100 mL Pyrex beaker containing 50 mL of neat propylene glycol was added 250 mg of MMC which was dissolved by sonication for 5 minutes. The solution was then filtered through a 0.5 micron Millex-SR filter (Millipore Corp., P/N#SLSR025NS). One mL portions of this solution were added to 8.2 mL Type I amber glass vials. The vials were purged with nitrogen, stoppered with West No. 1888 gray butyl stoppers, and sealed with aluminum caps. This solution was then placed on stability at different temperatures.

This solution retained 91.2% potency after one month at 40° C., 99.4% after three months at 25° C., and 98.6% after six months at 4° C. This solution has a predicted shelf-life ($\leq$10% potency loss) of at least 24 months at refrigerated temperature.

EXAMPLE 2

Using the procedure of Example 1, a 4.81 mg/mL solution of MMC was prepared in 95% PG in water. This solution retained 89.8% potency after one month at 40° C., 98.1% after three months at 25° C., and 100% after six months at 4° C. This solution has a predicted shelf-life ($\leq$10% potency loss) of at least 24 months at refrigerated temperature.

EXAMPLE 3

Using the procedure of Example 1, a 4.85 mg/mL solution of MMC was prepared in 90% PG in water. This solution retained 87.2% potency after one month at 40° C., 99.0% after three months at 25° C., and 99.2% after six months at 4° C. This solution has a predicted shelf-life ($\leq$10% potency loss) of at least 24 months at refrigerated temperature.

EXAMPLE 4

Into a 30 mL Pyrex beaker containing a mixture of 5 mL of Sterile Water for Injection and 5 mL of propylene glycol was added 50 mg of MMC which was dissolved by sonication for 5 minutes. The solution was then filtered through a 0.5 micron Millex-Sr filter (Millipore Corp., P/N#SLSR025NS). One mL portions of this solution were added to 10 mL Type I amber glass vials. The vials were purged with nitrogen, stoppered with West No. 1888 gray butyl stoppers, and sealed with aluminum caps. This solution was then placed on stability at different temperatures.

This solution retained 89.0% potency after two weeks at 40° C., and 90.2% after one month. This solution is expected to have a predicted shelf-life ($\leq$10% potency loss) of at least 24 months at refrigerated temperature.

EXAMPLE 5

Into a 50 mL Erlenmeyer flask containing 25 mL of neat propylene glycol was added 25 mg sodium bicarbonate. The mixture was stirred for 10 minutes. After standing for 30 minutes, the mixture was then filtered through a Millex-SR filter (Millipore Corp., P/N#SLSR025NS) to remove undissolved sodium bicarbonate. Apparent pH of propylene glycol before and after the treatment (after 1:10 dilution with water) was measured and were 6.5 and 8.4, respectively.

Into a 30 mL Pyrex beaker containing 10 mL of filtrate propylene glycol (pretreated with sodium carbonate) was added 50 mg of MMC which was dissolved by sonication for 5 minutes. The solution was then filtered through a 0.5 micron Millex-SR filter (Millipore Corp., P/N#SLSR025NS). 0.9 mL portions of this solution were added to 10 mL Type I amber glass vials. The vials were purged with nitrogen, stoppered with West No. 1888 gray butyl stoppers, and sealed with aluminum caps. This solution was then placed on stability at different temperatures.

This solution retained 97.0% potency after three months at 40° C., and full potency after three months at 25° C. This solution is expected to have a predicted shelf-life ($\leq$10% potency loss) of at least 24 months at refrigerated temperature.

REFERENCES

1. J. H. Beijnen et al., "Mitomycin antitumor agents: a review of their physico-chemical and analytical properties and stability", J. Pharm. & Biomed. Anal., 4: 275-295 (1986).

2. J. H. Beijnen et al., "Mitomycin C" in analytical Profiles of Drug Substances, 16: 361-401 (1987).

3. J. H. Beijnen et al., "A systematic study on the chemical stability of mitomycin A and mitomycin B", Chem. Pharm. Bull., 34: 2900-2913 (1986).

4. E. R. Garrett, "The physical chemical characterization of the products, equilibria, and kinetics of the complex transformations of the antibiotic porfiromycin", J. Med. Chem., 6: 488-501 (1963).

5. C. L. Stevens et al., "Chemistry and Structure of Mitomycin C", J. Med. Chem., 8: 1-10 (1965).

6. D. Edwards et al., "Determination of the stability of mitomycin C by high performance liquid chromatography", Int. J. Pharm., 4: 21-26 (1979).

7. J. H. Beijnen et al., "Degradation of mitomycin C in acid phosphate and acetate buffer solutions", Int. J. Pharm., 32: 111-121 (1986).

8. W. J. M. Underberg and H. Lingeman, "Aspects of the chemical stability of mitomycin and porfiromycin in acidic solution", J. Pharm. Sci., 72: 549-553 (1983).

9. L. M. L. Stolk et al., "Stability after freezing and thawing of solutions of mitomycin C in plastic minibags for intravesical use", Pharm. Weekblad Sci. Ed., 8: 286-288 (1986).

10. J. H. Beijnen et al., "Stability of mitomycins in infusion fluids", Arch. Pharm. Chem. Sci. Ed., 13: 58–66 (1985).

11. E. J. Quebbman et al., "Stability of mitomycin admixtures", Amer. J. Hosp. Pharm., 42: 1750–1754 (1985).

12. "Mutamycin", Physicians' Desk Reference, 42nd Ed., Medical Economics Co., 1988, p. 776–777.

What is claimed is:

1. A composition comprised of a stable solution of Mitomycin C in a solvent medium consisting of from about 50–90% (v/v) propylene glycol and from about 10–50% (v/v) water.

2. A composition according to claim 1 wherein the concentration of Mitomycin C ranges from about 0.5 mg/mL to about 12 mg/mL.

3. A composition according to claim 1 or claim 2 wherein the solvent medium consists of from about 60–90% (v/v) propylene glycol and from about 10–40% (v/v) water.

4. A composition according to claim 1 wherein the propylene glycol has undergone pretreatment with a pharmaceutically acceptable base.

5. A composition according to claim 4 wherein the propylene glycol has undergone pretreatment with sodium bicarbonate.

6. A composition according to claim 1, 2, 3, 4 or 5 diluted with a parenteral vehicle suitable for sterile parenteral administration.

* * * * *